US006647804B1

(12) United States Patent
Deines (10) Patent No.: US 6,647,804 B1
(45) Date of Patent: Nov. 18, 2003

(54) SYSTEM AND METHOD FOR FLOW MEASUREMENT IN A PIPE

(75) Inventor: Kent L. Deines, Poway, CA (US)

(73) Assignee: RD Instruments, Inc., San Diego, CA (US)

( * ) Notice: Subject to any disclaimer, the term of this patent is extended or adjusted under 35 U.S.C. 154(b) by 0 days.

(21) Appl. No.: 09/501,826

(22) Filed: Feb. 10, 2000

Related U.S. Application Data
(60) Provisional application No. 60/119,493, filed on Feb. 10, 1999.

(51) Int. Cl.[7] .................................................. G01F 1/86
(52) U.S. Cl. .................... 73/861.18; 73/1.16; 73/861.23
(58) Field of Search ........................ 73/861.18, 861.25, 73/861.23, 861.27, 861, 1.16

(56) References Cited

U.S. PATENT DOCUMENTS

| | | | | |
|---|---|---|---|---|
| 4,083,246 A | | 4/1978 | Marsh | 73/227 |
| 4,365,829 A | | 12/1982 | Fowler | 285/162 |
| 4,386,409 A | | 5/1983 | Petroff | 364/510 |
| 4,397,191 A | | 8/1983 | Forden | 73/861.18 |
| 4,452,090 A | * | 6/1984 | Kou et al. | 73/861.28 |
| 4,484,478 A | | 11/1984 | Härkönen | 73/861.06 |
| 4,742,717 A | * | 5/1988 | Ichino | 73/861.18 |
| 4,754,650 A | * | 7/1988 | Smalling et al. | 73/861.28 |
| 4,787,252 A | * | 11/1988 | Jacobson et al. | 73/861.28 |
| 4,823,612 A | * | 4/1989 | Ichino | 73/861.18 |
| 4,928,534 A | * | 5/1990 | Ichino | 73/861.18 |
| 5,020,374 A | | 6/1991 | Petroff et al. | 73/861.25 |
| 5,179,862 A | * | 1/1993 | Lynnworth | 73/861.28 |
| 5,251,490 A | * | 10/1993 | Kronberg | 73/861.25 |
| 5,277,070 A | * | 1/1994 | Dorr | 73/861.28 |
| 5,329,821 A | * | 7/1994 | Birnbaum et al. | 73/861.28 |
| 5,421,211 A | * | 6/1995 | Heckman | 73/861.25 |
| 5,515,733 A | * | 5/1996 | Lynnworth | 73/861.27 |
| 5,615,173 A | * | 3/1997 | Brumley et al. | 367/90 |
| RE35,535 E | | 6/1997 | Brumley et al. | 367/90 |
| 5,808,195 A | * | 9/1998 | Byrd | 73/215 |
| 5,821,427 A | * | 10/1998 | Byrd | 73/861.25 |
| 5,880,377 A | * | 3/1999 | Celik | 73/861.22 |
| 5,896,885 A | | 4/1999 | Svetlik | 137/15 |
| 5,967,567 A | | 10/1999 | Nordstrom | 285/139.1 |
| 6,378,357 B1 | * | 4/2002 | Han et al. | 73/54.41 |

OTHER PUBLICATIONS

"Acoustic Measurement of River Discharge".
R. Lee Gordon, Journal of Hydraulic Engineering, vol. 115, No. 7, pp. 925–936 (Jul., 1989).

* cited by examiner

Primary Examiner—Edward Lefkowitz
Assistant Examiner—Andre Allen
(74) Attorney, Agent, or Firm—Knobbe, Martens, Olson & Bear LLP (57) ABSTRACT

Fluid flow in a conduit is measured with an acoustic Doppler system installed in an opening in the pipe. The Doppler system may include transducers and driving circuitry to produce narrow beam pulses of acoustic energy. The transducers may be coupled to an acoustic refractive lens which is sealed in the opening.

10 Claims, 8 Drawing Sheets

SYSTEM AND METHOD FOR FLOW MEASUREMENT IN A PIPE

CROSS REFERENCE TO RELATED APPLICATIONS

This application claims priority under 35 U.S.C. §119(e) to Provisional Application Ser. No. 60/119,493, entitled SYSTEM AND METHOD FOR MEASURING FLUID FLOW USING A SONAR SYSTEM, and filed Feb. 10, 1999. The content of Provisional Application Serial No. 60/119,493 is hereby incorporated by reference in its entirety.

BACKGROUND OF THE INVENTION

1. Field of the Invention

The invention relates to flow velocity measurements in pipes and conduits carrying water, sewage, and other fluids.

2. Description of the Related Art

There are many environments where information regarding the mass and/or volume flow rate of a fluid through a conduit is valuable. These include irrigation, residential water distribution, sewage treatment, and many others. Although various types of mechanical flow meters have been used, acoustic methods are often preferable because of their ease of installation, lack of interference with the flow, and long term reliability. One type of acoustic flow measurement device utilizes the Doppler effect to measure flow speed. With these devices, sound energy is reflected off of particles moving with the flowing fluid and is received by a receiving transducer. Sound energy received by the receiving transducer is frequency shifted due to the relative motion between the particles and the receiving transducer. The frequency shift is related to the flow rate of the fluid.

Several systems using Doppler effect based flow measurement have been proposed. One such system is described in U.S. Pat. No. 5,020,374 to Petroff et al. With the system described in this patent, separate transmit and receive transducers are placed in the fluid flow, and a continuous wave signal is output from the transmit transducer. Because the transducers are placed within the flow, installation is difficult and labor intensive, especially if installation is desired in a conduit with fluid flow already present. Furthermore, due to its continuous wave nature and the fact that the Petroff et al. device produces a quickly spreading beam of acoustic energy, an accurate measurement of even an overall average fluid velocity in the pipe is at best difficult and often impossible to obtain. There is therefore a need to develop flow measurement techniques which are more accurate than have been previously available.

SUMMARY OF THE INVENTION

With embodiments of the present invention, flow rates of fluid flowing through pipes or other conduits are measured in a relatively convenient and accurate manner. In one embodiment, the invention comprises an assembly for routing fluid and measuring a flow rate of the fluid. The assembly comprises a conduit comprising a wall defining a fluid flow path, said wall having an opening therein, an acoustic transducer assembly sealed into said opening and a signal generator coupled to said acoustic transducer assembly and configured to electrically drive said acoustic transducer assembly.

In another embodiment, an apparatus for measuring the flow rate of fluid in a pipe comprises an acoustic lens, a plurality of acoustic transducers coupled to a lens so as to emit acoustic energy through a surface of the lens, and a signal generator configured to electrically drive the acoustic transducers at a selected excitation frequency so as to produce sound waves in the fluid having a selected wavelength, wherein the acoustic transducers have a characteristic dimension that is much larger than the selected wavelength.

Methods of fluid flow measurement are also provided. In one embodiment, such a method comprises positioning a plurality of acoustic transducers in an opening in the wall of the pipe, emitting a plurality of narrow beam pulses of acoustic energy into fluid flowing within the pipe using the transducers, detecting doppler shifted reflections of acoustic energy from regions within the fluid, and determining total fluid flow through the pipe at least in part by analyzing the doppler shifted reflections.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
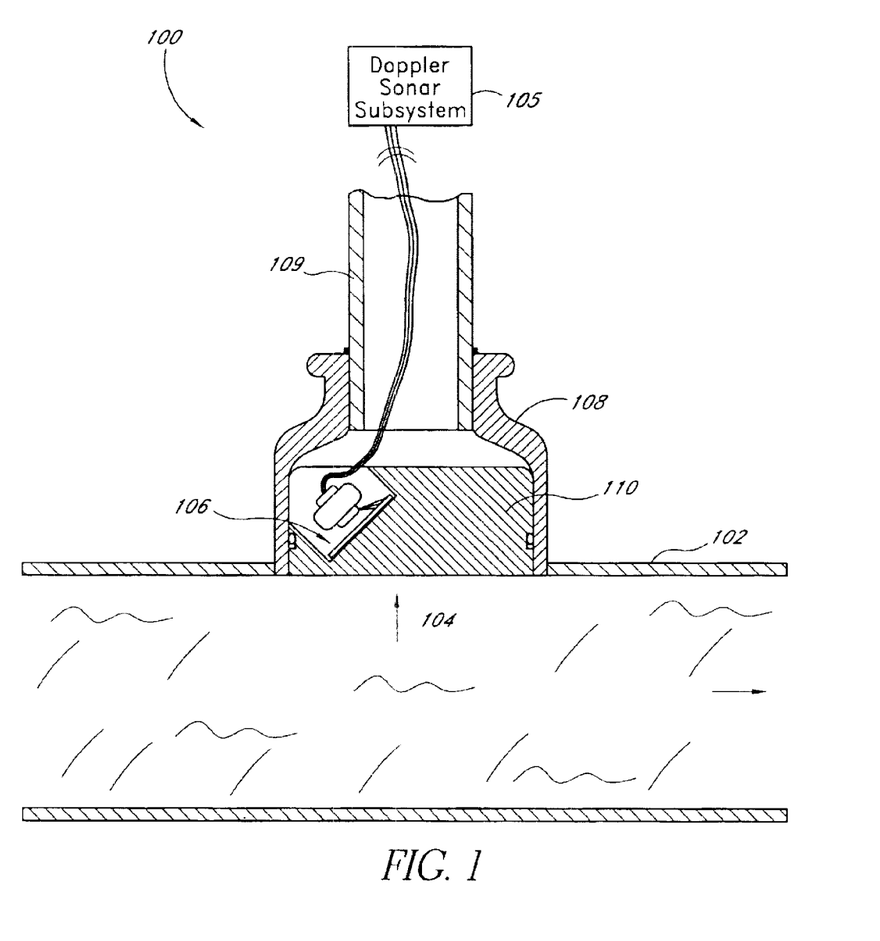
FIG. 1 is a side cross-sectional view of a first embodiment of the fluid flow measuring system of the present invention installed in a fluid-carrying pipe.

FIG. 1 is a cross-sectional view of a first embodiment of the flow measuring system 100 of the present invention. While the system is depicted as being installed in a pipe 102, it can be appreciated that the system 100 may be employed to measure flow in other mediums for conveying fluids including, for example, open channels or ducts. The system 100 is generally includes a transducer array 104 having one or more piezoelectric transducer elements 106 and an acoustic lens 110 (both shown in FIG. 2) connected to an acoustic Doppler sonar subsystem 105. The transducer array 104 is contained within a transducer housing 108 which acts as a partial pressure boundary for the fluid in the pipe. The housing 108 may be mated to the pipe 102 using any fastening technology which will maintain the leak-tight integrity of the system, such as mechanical threads, welding, brazing or adhesive. A sealed pipe 109 is fitted within the top portion of the housing 108, and acts as a conduit for the electrical cabling associated with the transducer array elements. It will be recognized that any number of techniques for sealing the end of the pipe 109 may be used, including a sealed penetration, a water-tight grommet, or even a static fluid head (water seal).

In the embodiment of FIG. 1, a pulsed broadband Acoustic Doppler Current Profiler (ADCP) such as the "Workhorse Sentinel" manufactured by Rowe-Deines Instruments, Inc. of San Diego, Calif., is used in conjunction with the transducer array to generate acoustic signals having a nominal frequency of 2.4 MHz for transmission and analyze received acoustic signals, thereby providing information relating to the fluid velocity and mass flowrate Q within the pipe. The construction and operation of the Rowe-Deines acoustic Doppler sonar system is described in U.S. Pat. No. Re. 35,535 entitled "Broadband Acoustic Doppler Current Profiler", which is incorporated by reference herein in its entirety. Of course, other types and configurations of sonar systems may be used to generate and/or analyze the signals applied to or generated by the transducer array. For example, a narrowband Doppler or continuous wave (CW) sonar system could be substituted in place of the aforementioned broadband ADCP in certain circumstances.

The mass flowrate (Q) of the fluid in the conveyance medium can be determined through analysis of the fluid velocity information provided by the array/ADCP, since the pulsed ADCP system affords superior range cell resolution. In one embodiment, the determination of mass flowrate is made through the use of a computer algorithm running on a microcomputer system or processor which models the flow in the medium as being essentially symmetric around the center point of the flow area. For example, in a circular pipe, flow is modeled to be symmetric around the central longitudinal axis of the pipe, with the flow velocity varying with distance r from the center point according to a function f (r). Note that the function f (r) may be either empirically determined via velocity information obtained by the ADCP from multiple range cells, or mathematically modeled based on the measurement of one range cell within the pipe. The flow velocity is then averaged or integrated over the cross-section of the pipe to provide a figure representative of the average flow velocity in the pipe. This total flow velocity can then be used to calculate the average flow volume per unit time (Q), which may be multiplied by the known or measured density of the fluid to determine the mass flowrate. While the above-described computer algorithm and processor is used in the present embodiment to correlate the velocity profile data to a mass flowrate, it can be appreciated that other techniques and analytical methods may be used.

Figure 4:
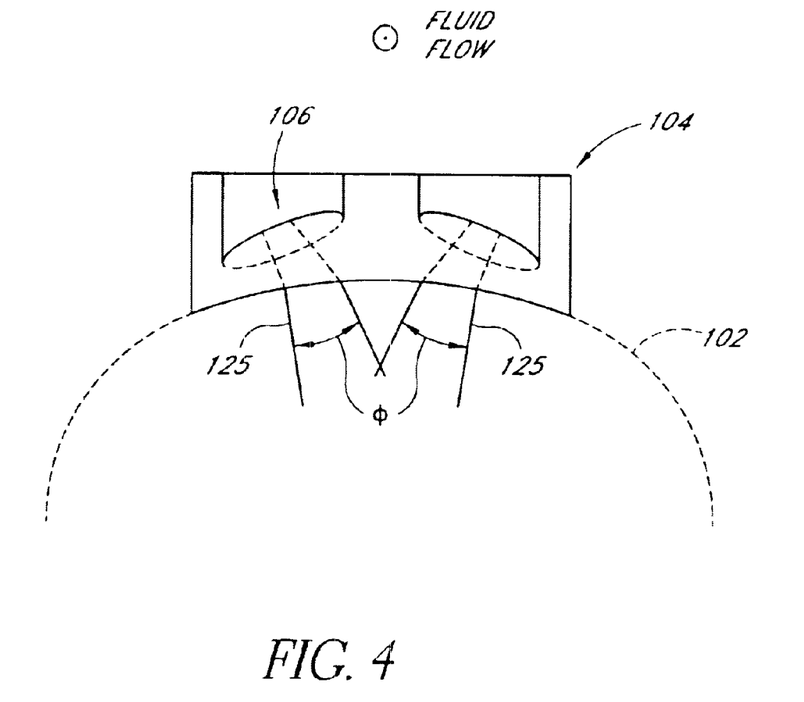
FIG. 4 is a cross-sectional view of the transducer array of FIG. 2 taken along line 4—4, illustrating the curvature of the lens.

The embodiment of FIG. 1 also uses a refractive acoustic lens 110 as part of the array 104. An example lens is described in expired U.S. Pat. No. 4,063,214 assigned to Sperry Rand Corporation, which is incorporated by reference herein in its entirety, although other configurations may be used based on the particular application. In the present embodiment, the lens is manufactured from Rexolite (a polymer) which is chosen for its compatible acoustic properties, resistance to various types of fluids, and ruggedness. The lens 110 may be made to conform with the interior surface of the pipe as shown in FIGS. 1 and 4 so as to minimize fluid turbulence, which unchecked will lead to spurious noise and flow resistance. However, it will also be recognized that the vertical (i.e., radial) position of the transducer array 104 and lens 110 may be varied to provide various desired properties and performance.

Figure 2:
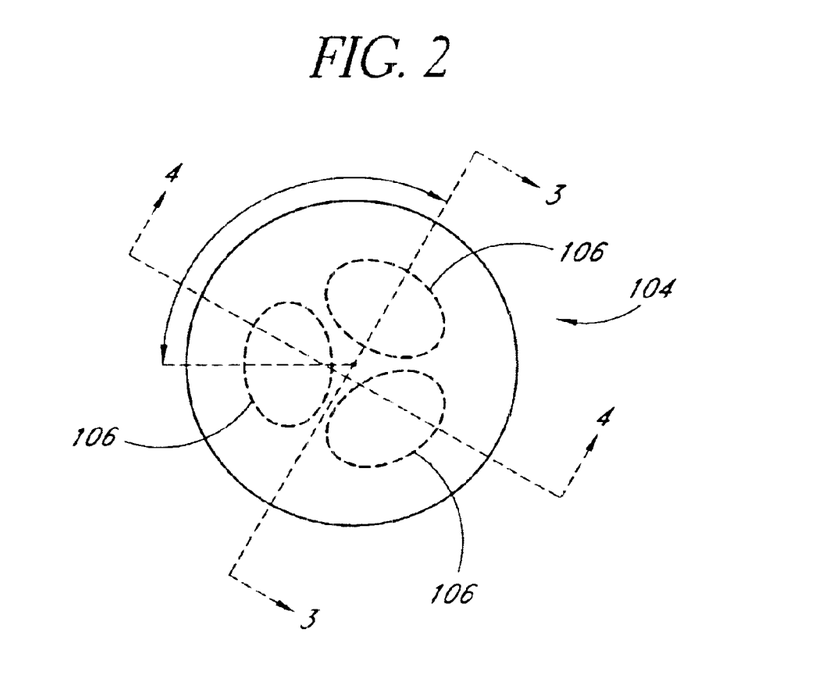
FIG. 2 is a bottom plan view of the transducer array of the measuring system of FIG. 1, illustrating the relative arrangement of the individual transducer elements.

FIG. 2 is a bottom plan view of a first embodiment of the transducer array 104 of the present invention. This bottom view corresponds with the portion of the array 104 which is closest to the fluid in the pipe and through which acoustic beams are transmitted. The transducer array of FIG. 2 results in the formation of three acoustic beams oriented 120 degrees apart (not shown) as measured in the plane of the array. Each of these three beams has a comparatively narrow beam dispersion angle ($\phi$) of approximately 2.5 degrees, which facilitates spatial localization of the fluid velocity measurements. Note that in the present embodiment, approximately 25 wavelengths ($\lambda$) are required to generate this desired beam dispersion. Accordingly, based on a nominal wave propagation velocity of 1500 m/s through the fluid, which in one embodiment is assumed to be predominantly water, and an acoustic frequency of 2.4 MHz, transducer elements having a diameter of roughly 15 mm are required. Therefore, to comfortably fit three transducers in close proximity as shown in FIG. 2, and using the exemplary dimensions, a total array diameter must be on the order of 1.75 inches.

Figure 3:
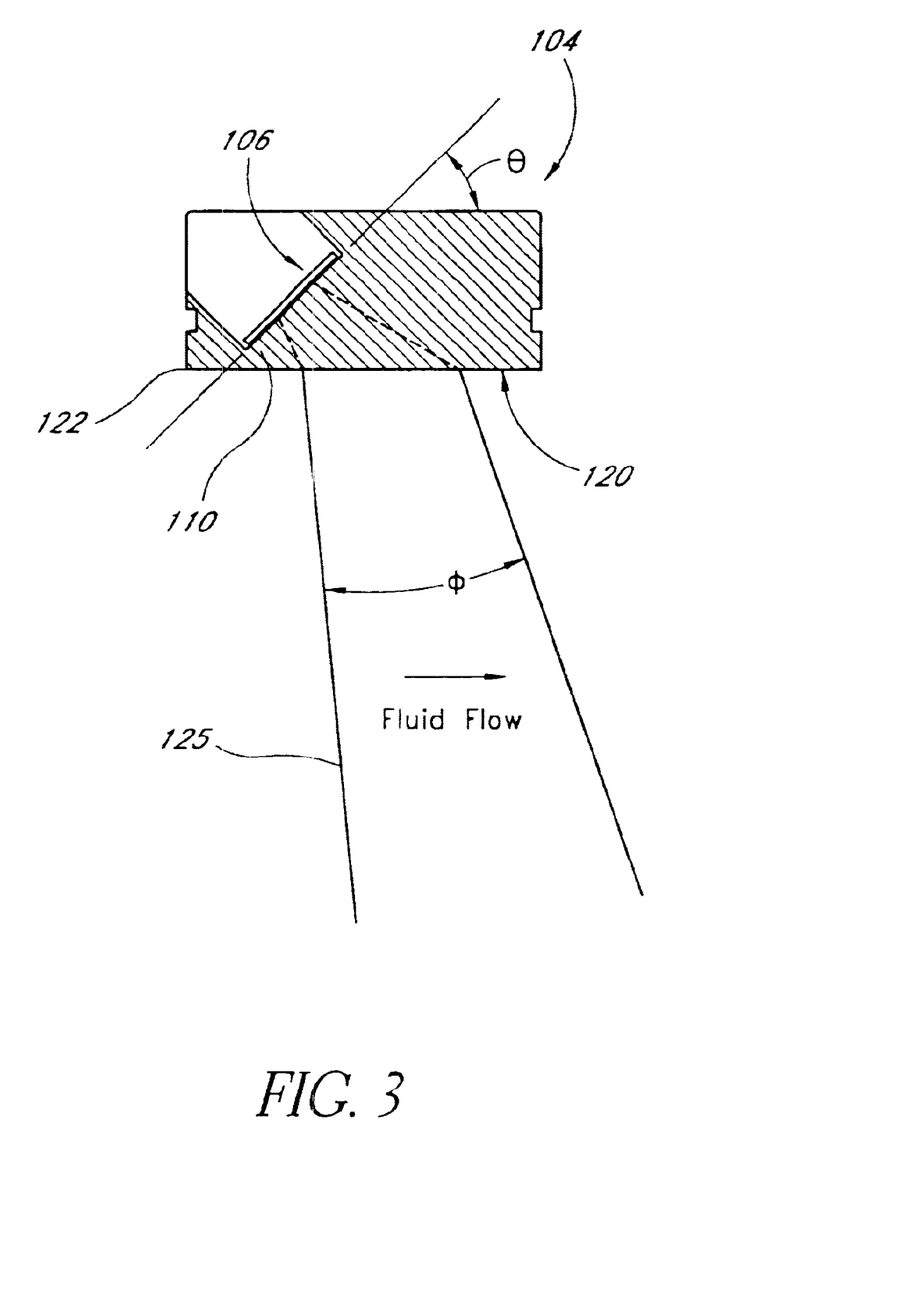
FIG. 3 is cross-sectional view of the lens element of the transducer array of FIG. 2 taken along line 3—3, illustrating the arrangement of an individual transducer element with respect to the lens element.

FIG. 3 illustrates the general relationship of the piezoelectric transducer elements to the lens element 110 in the transducer array of FIG. 2. As shown in FIG. 3, the piezoelectric elements, which in one embodiment are formed from ceramic, are each oriented at a non-zero angle ($\theta$) to the bottom plane of the lens 120. As the acoustic energy radiated/received by the elements crosses the lens/fluid boundary 122, it is refracted according to Snell's law as shown in FIG. 3. The angle $\theta$, material, and thickness of the lens may be chosen to produce the desired acoustic refraction and dispersion of the beam 125. Furthermore, the speed of sound of the fluid being carried in the pipe 102 does not need to be known.

Figure 5:
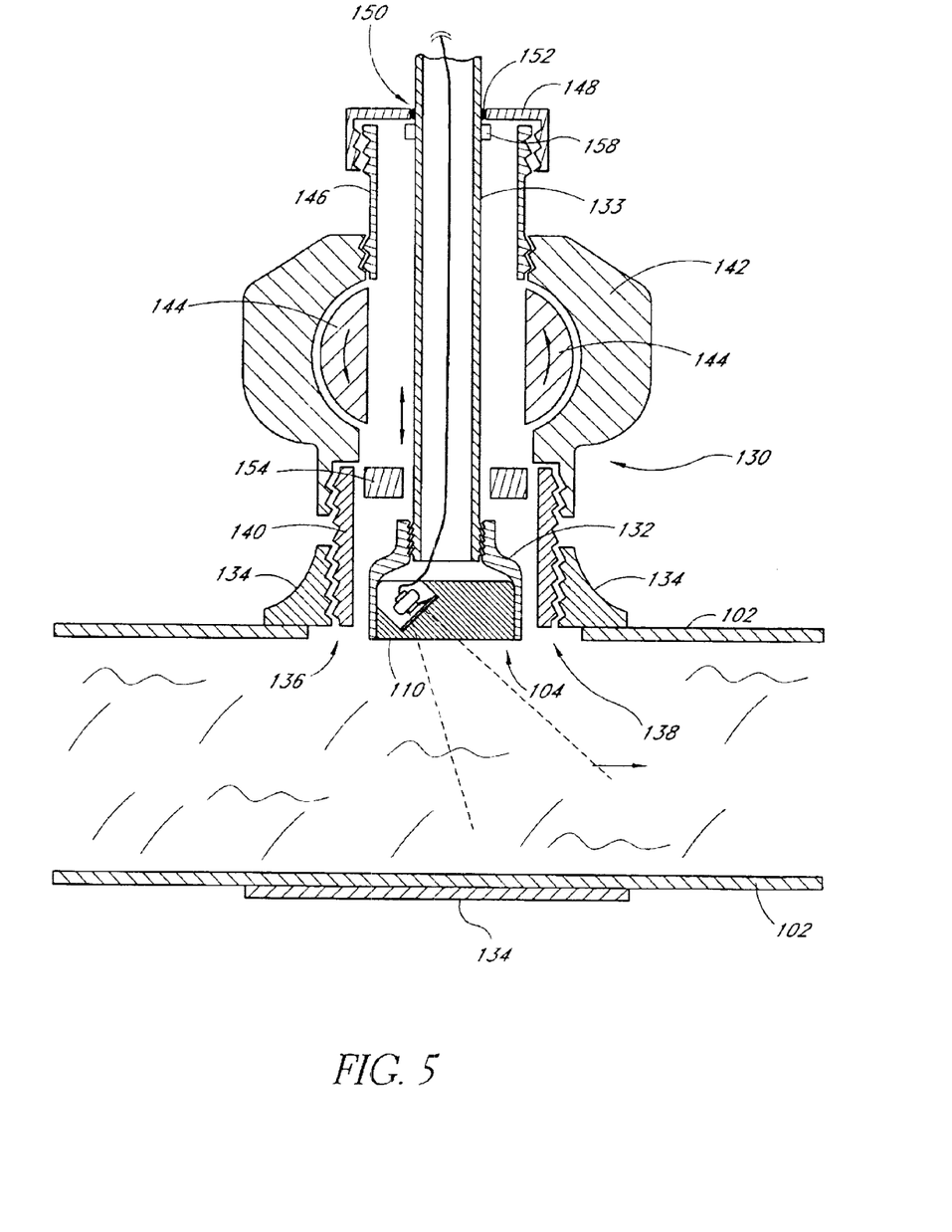
FIG. 5 is side cross-sectional view of a second embodiment of the flow measuring system of the present invention.

FIG. 5 illustrates another embodiment of the flow measuring system of the present invention. In this embodiment, the transducer array 104 is contained wholly within a multi-piece transducer housing assembly 130 which is oriented so as to be substantially normal to the flow axis of the pipe, although other orientations are possible. Here, the assembly 130 as a whole is chosen to have an inside diameter (I.D.) of approximately 43 mm based on the array size as discussed above. As shown in FIG. 5, the array is contained within a reducer 132 which has been sized to both receive the array 104 and Rexolite lens 110 on its interior, and fit within the inside diameter of the assembly 130 on its outside dimension. A routing pipe 133 of outside diameter approximating 0.5 in. (standard ½ in. brass pipe is used in the present embodiment) is threaded into the top portion of the reducer 132, thereby facilitating routing of the electrical cables associated with the array 104. The routing pipe 133 may optionally be sealed at its distal end (not shown) so as to permit the passage of the electrical cabling, but minimize or eliminate the flow of fluid there around should gross leakage past the transducer array occur.

In the present embodiment, the housing assembly 130 is comprised of a saddle 134 having an opening 136 of circular cross-section rigidly mounted around the periphery of the pipe 102 coincident with the perforation 138 through the wall of the pipe 102. A nipple 140 is threaded into the opening 136 in the saddle 134, and a valve 142 threaded onto the nipple 140. The valve may be of any type including (e.g., gate, ball, or other) which provides an internal aperture through its sealing member 144 which has an inside diameter sized to permit passage of the array 104 and reducer 132. A pipe section 146 having an inside diameter of roughly 2 in. is threaded into the top portion of the valve 142 as shown in FIG. 5. Lastly, a cap 148 having an aperture 150 sized to receive the routing pipe 133 is threaded or mounted on the top portion of the pipe section 146, thereby completing the housing assembly 130. The cap 148 includes a sealing mechanism 152 such as an O-ring (shown in FIG. 5) or mechanical seal (not shown) to seal the routing pipe 133 against leakage around its exterior. A spacer ring 154 may also be included around the routing pipe 133 as shown to restrict lateral motion of the array 104 and lens 110 during installation and/or operation. A retaining device 158 is also positioned on the routing pipe 133 and fastened thereto to preclude fluid pressure within the pipe 102 from pushing the array 104 and routing pipe 133 upwards during operation. Other mechanical devices such as stops or keys (not shown) located within the assembly 130 and/or fluid pipe 102 may also be used to assist in orienting and locating the array 104 properly within the system 100 during installation or replacement.

It will be recognized that while the above-described embodiment includes various dimensions and components, any number of combinations of pipes, valves, and component diameters can be used depending on the particular application. For example, a single element transducer array having a smaller diameter may be used with a housing assembly 130 and reducer 132 of comparably smaller diameter. Similarly, the housing assembly 130 or its constituent components could be fabricated as a single, unitary component rather than being assembled as described herein. A wide range of possibilities for constructing the housing assembly 130 and associated components exists.

Figure 6:
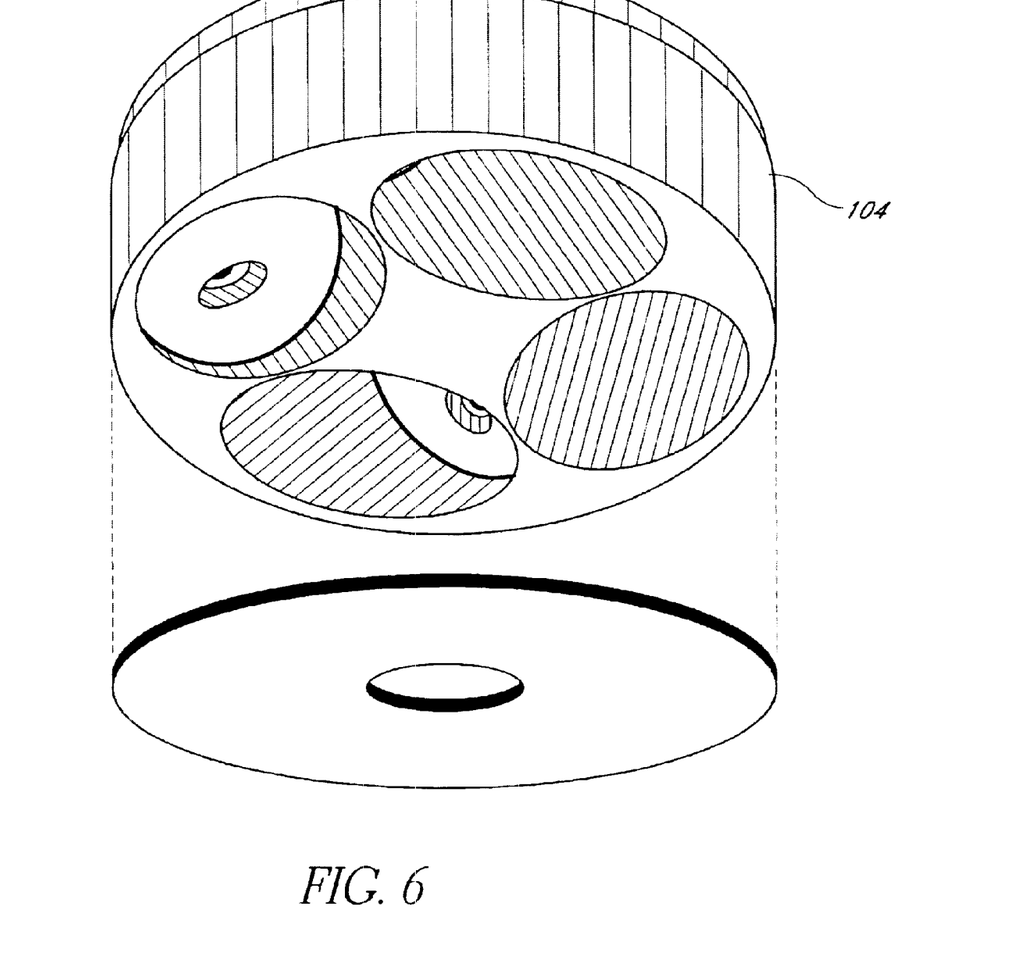
FIG. 6 is a top plan view of a second embodiment of the transducer array of the present invention, utilizing a pinwheel configuration.

FIG. 6 illustrates a second embodiment of the transducer array 104 of the present invention. Specifically, in this embodiment, a "pinwheel" type array geometry is used. The construction and operation of the pinwheel array is described in detail in co-pending U.S. patent application Ser. No. 09/082,500 entitled "Pinwheel Transducer Array", filed May 21, 1998 and assigned to Rowe-Deines Instruments, Inc. of San Diego, Calif., which is incorporated herein by reference in its entirety.

Figure 7:
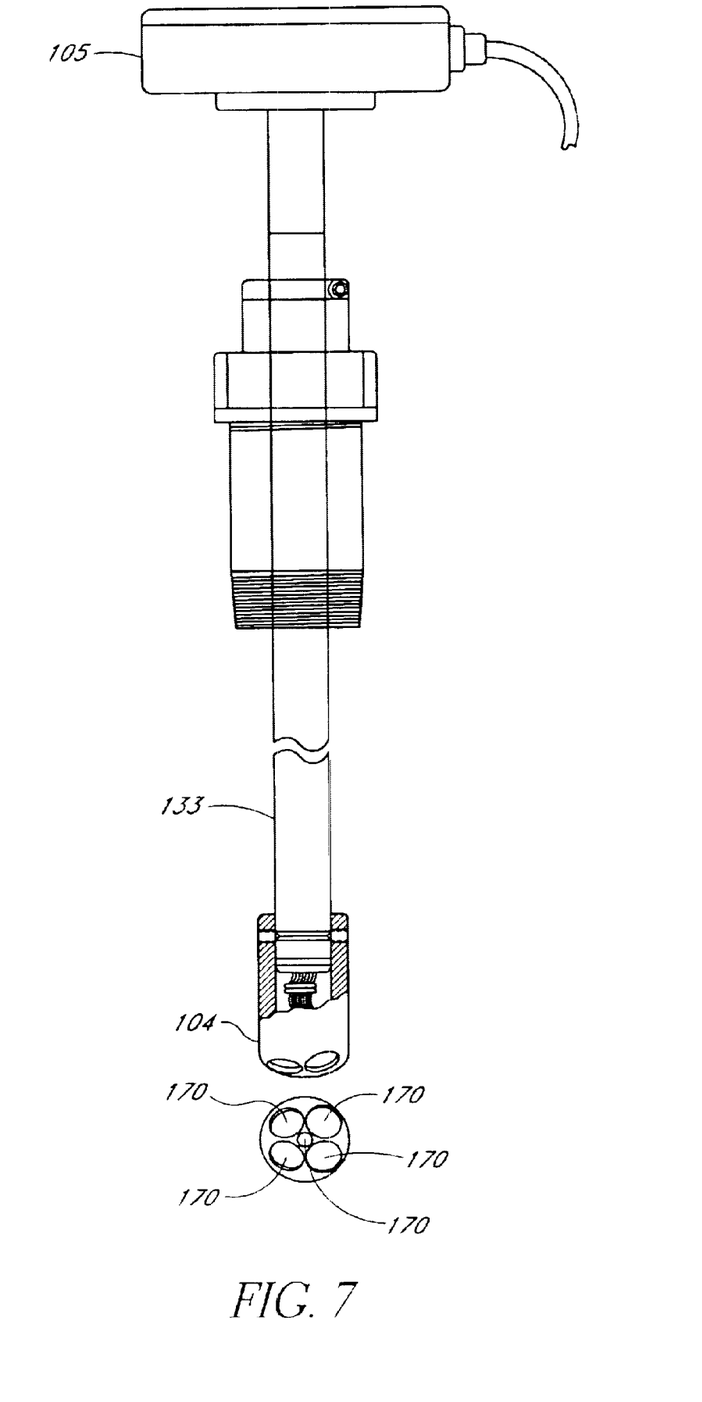
FIG. 7 is a plan view of a third transducer array embodiment utilizing a Janus configuration.

A third transducer array 104 is illustrated in FIG. 7. This is an array of five transducers, one vertical, and the other four at an angle to the flow direction. The vertical transducer may be used to measure the diameter of the pipe. In this embodiment, the lens is configured with a set of recessed facets 170 corresponding to each one of the five transducers. It is further noted that while the embodiments of FIGS. 2, 6, and 7 are described specifically herein, other types of array configurations may be used in conjunction with the present invention.

Figure 8:
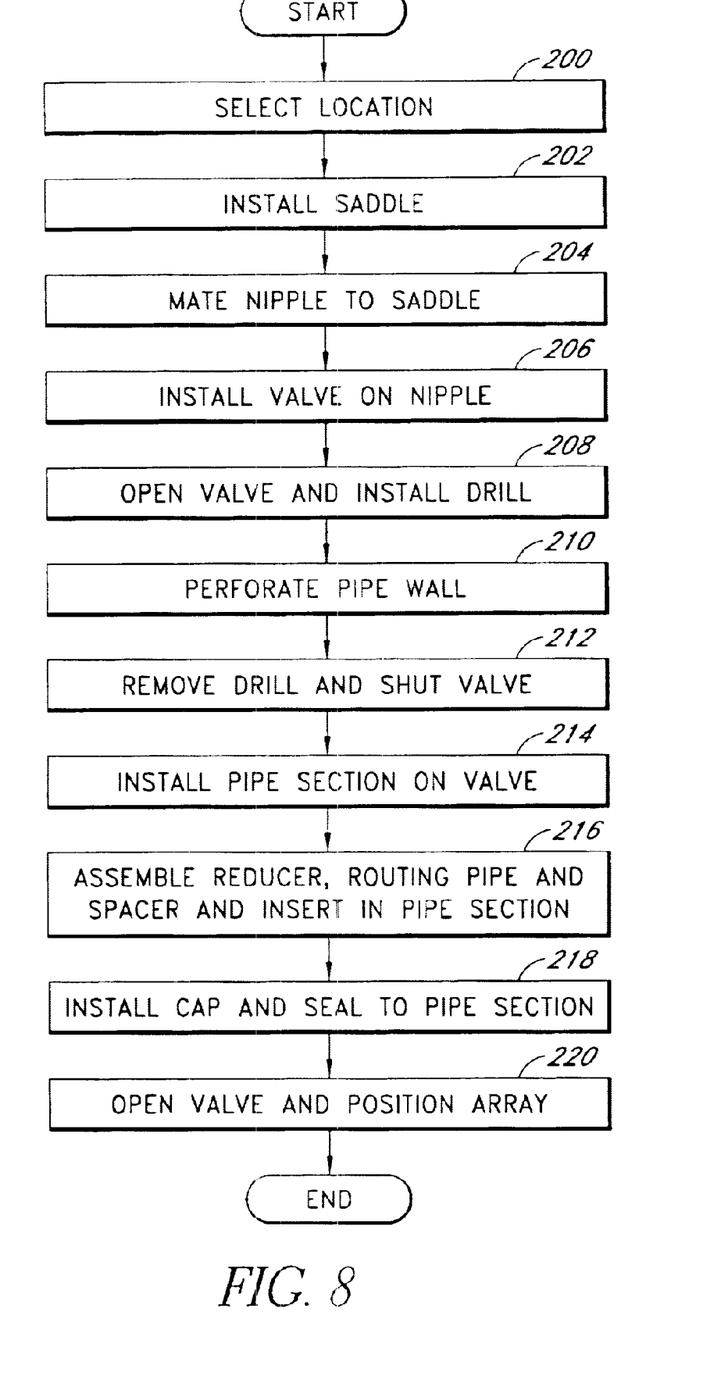
FIG. 8 is a flow chart illustrating one embodiment of the method for installing the transducer array of the present invention via a hot tap.

Referring now to FIG. 8, a method of installing the flow measuring system of the present invention in a pipe under fluidic pressure is described with respect to the embodiment of FIG. 5. As shown in FIG. 8, the pipe in which the system is to be installed (and optimal location therefor) is first selected in state 200. Next, the "saddle" 134 which encloses a portion of the pipe is installed over the desired area of installation in state 202. The saddle includes an access opening 136 which is later used to install and access the array. As previously described, the saddle is tightly fitted and sealed to the pipe around its circumference to inhibit leakage, and includes provision to receive a gate or other type of valve thereon, thereby allowing sealing of the access opening 136 as well.

After the saddle 134 has been installed, the nipple 140 is mated to the saddle in state 204. Next, in state 206, the valve is installed. A sealed drilling apparatus of the type well known in the mechanical arts is inserted into the access port through the gate valve in state 208. In state 210, the aforementioned drilling apparatus is used to perforate the wall of the pipe 102 in the desired diameter (i.e., approximately 2 in. using the embodiment of FIG. 5). In state 212, the drilling apparatus is removed, the valve 142 is shut. In state 214, the pipe section 146 is installed into the top of the valve 142. In state 216, the spacer ring 154 is installed over the routing pipe 133, followed by the sealing cap 154, and the array 104, reducer 132, routing pipe 133, and spacer ring 154 being positioned within the pipe section 146 up until the point of contact with the sealing element 144 of the valve 142. In state 218, the cap 154 is threaded or otherwise mounted to the pipe section 146 so as to form a seal. Lastly, in state 220, the valve 142 is opened (i.e., in FIG. 5, the ball 144 is rotated such that its aperture is aligned with the interior of the nipple 140 and pipe section 146) and the array 104, lens 110, reducer 132, spacer 154, and routing pipe 133 slid through the valve into place within the fluid pipe 102. The system 100 may then be tested and operated.

It will be recognized that while the foregoing discussion describes a preferred method for installing the transducer array within a fluid-carrying pipe under pressure, other sequences of acts may be used, and/or certain acts may be deleted from or added to the method as required by the particular application.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of installing an acoustic flow measurement device in a pipe containing fluid under pressure and using said device to measure a fluid flow rate in said pipe, the method comprising:

coupling an apparatus having an access opening around an outer surface of said pipe containing fluid under pressure;

coupling a valve to said apparatus, wherein said valve is configured to selectively block fluid flow;

perforating a portion of said pipe covered by said apparatus, such that said fluid flows through said perforated portion;

installing at least one acoustic transducer in said perforated portion of said pipe;

emitting at least one pulse of acoustic energy into said fluid flowing within said pipe with said at least one acoustic transducer;

detecting Doppler shifted reflections of acoustic energy from regions within said fluid; and determining total fluid flow through said pipe at least in part by analyzing said Doppler shifted reflections.

2. The method of claim 1, wherein said determining comprises determining fluid flow rates at a plurality of locations within said pipe.

3. The method of claim 1, wherein said at least one pulse has a beam dispersion of approximately 2.5 degrees.

4. An apparatus for measuring the flow rate of fluid in a pipe comprising:

an acoustic lens;

at least one acoustic transducer coupled to said lens so as to emit acoustic energy through a surface of said lens;

a signal generator configured to electrically drive said at least one acoustic transducer at a selected excitation frequency so as to produce pulsed sound waves in the fluid having a selected wavelength, wherein said at least one acoustic transducer has a characteristic dimension that is much larger than said selected wavelength so as to form a narrow beam of emitted acoustic energy; and a processor configured to determine a velocity profile comprising a plurality of velocity measurements of said fluid at a plurality of locations within said pipe.

5. The apparatus of claim 4, wherein said surface is contoured as a smooth semi-circular arc.

6. The apparatus of claim 4, wherein said surface comprises a plurality of substantially flat facets.

7. The apparatus of claim 6, wherein said facets are recessed.

8. The apparatus of claim 4, wherein said characteristic dimension is approximately 25 times said selected wavelength.

9. The apparatus of claim 4, wherein said selected frequency is approximately 2.4 MHz.

10. The apparatus of claim 9, wherein said characteristic dimension is approximately 15 mm.

* * * * *